United States Patent
Luong

(10) Patent No.: US 9,933,374 B2
(45) Date of Patent: Apr. 3, 2018

(54) DEVICE FOR MEASURING THE QUALITY FACTOR OF A CAVITY, IN PARTICULAR A SUPERCONDUCTING CAVITY PERTURBED BY RESONANT ELECTRON DISCHARGES

(71) Applicant: COMMISSARIAT A L'ENERGIE ATOMIQUE ET AUX ENERGIES ALTERNATIVES, Paris (FR)

(72) Inventor: Michel Luong, Sceaux (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 573 days.

(21) Appl. No.: 14/491,053

(22) Filed: Sep. 19, 2014

(65) Prior Publication Data

US 2015/0108999 A1   Apr. 23, 2015

(30) Foreign Application Priority Data

Sep. 20, 2013 (FR) ...................... 13 59059

(51) Int. Cl.
  *G01N 22/00* (2006.01)
  *G01R 27/26* (2006.01)
  (Continued)

(52) U.S. Cl.
  CPC ............. *G01N 22/00* (2013.01); *G01N 27/22* (2013.01); *G01R 21/00* (2013.01); *G01R 27/26* (2013.01);
  (Continued)

(58) Field of Classification Search
  CPC ........ G01N 22/00; G01N 27/22; G01R 27/26; H01P 5/04; H01P 5/103; H01P 7/06
  (Continued)

(56) References Cited

U.S. PATENT DOCUMENTS 4,642,571 A * 2/1987 Minami .................... H01P 5/04
                                                      307/106
5,319,313 A * 6/1994 Vogel ....................... H05H 7/02
                                                      315/5.41

FOREIGN PATENT DOCUMENTS

FR         2 718 247        10/1995

OTHER PUBLICATIONS

Search Report and Written Opinion issued for French Patent Application No. 1359059, dated Jun. 19, 2014.
(Continued)

*Primary Examiner* — Melissa Koval
*Assistant Examiner* — Courtney McDonnough
(74) *Attorney, Agent, or Firm* — Pillsbury Winthrop Shaw Pittman LLP

(57) ABSTRACT

A device for measuring the unloaded quality factor of a resonant cavity which has an input port to accept incident power and an output port to measure the dissipated power, wherein the device includes: a transmission line designed to be coupled to the input port of the resonant cavity to be characterized, which has a coupling coefficient $\beta_i$ and which is designed to transmit an incident power generated by a power generator; a switch located upstream of the transmission line at a distance from the cavity which is equivalent to $(2n+1)\lambda_g/4$, where n is a whole number equal to or greater than zero and $\lambda_g$ the wavelength of the wave guided by the transmission line, the switch allowing the coupling coefficient $\beta_i$ at the input port to the cavity to be modified at the time of the measurement of the unloaded quality factor of the cavity.

8 Claims, 1 Drawing Sheet

(51) Int. Cl.
- *H01P 5/04* (2006.01)
- *G01N 27/22* (2006.01)
- *G01R 21/00* (2006.01)
- H01P 5/103 (2006.01)
- H01P 7/06 (2006.01)

(52) U.S. Cl.
CPC ............... *H01P 5/04* (2013.01); *H01P 5/103* (2013.01); *H01P 7/06* (2013.01)

(58) Field of Classification Search
USPC ........................................................ 324/636
See application file for complete search history.

(56) References Cited

OTHER PUBLICATIONS

J. Knobloch, "Basic Concepts of Measurements Made on Superconducting RF Cavities", Laboratory of Nuclear Studies, Cornell University, Aug. 30, 1991, XP055123352.

* cited by examiner

DEVICE FOR MEASURING THE QUALITY FACTOR OF A CAVITY, IN PARTICULAR A SUPERCONDUCTING CAVITY PERTURBED BY RESONANT ELECTRON DISCHARGES

CROSS-REFERENCE TO RELATED APPLICATIONS

This application claims priority to French Patent Application No. 1359059, filed Sep. 20, 2013, the entire content of which is incorporated herein by reference in its entirety.

FIELD

The field of the invention is that of characterization of resonators (or resonant cavities) under vacuum, which exhibit very low losses and which are liable to perturbation by resonant electron discharges.

The invention applies in particular to high-frequency resonant cavities constructed from superconducting materials.

The present invention relates more specifically to a device for measuring the quality factor $Q_0$, which is equivalent to the unloaded quality factor of a resonant cavity, defined as the ratio of the energy stored to the power dissipated, multiplied by the pulsatance $\omega_0$ (also called the angular frequency) at resonance.

BACKGROUND

In a resonant cavity, power may be dissipated both in the materials enclosed within resonator, usually dielectrics, as well as over the walls. It is possible therefore to respectively measure the complex permittivity of the dielectrics and/or the surface resistance of the conductors forming the walls of the resonant cavity.

In certain situations, since these characteristics are liable to vary as a function of the stored energy it is necessary to measure the quality factor $Q_0$ at different electromagnetic field amplitudes. In the case of superconducting resonant cavities, used for example to accelerate particle beams, the measurement of $Q_0$ as a function of the accelerating gradient (electric field) up to the sudden transition from a superconducting material to the normal conduction state (known as "quench") represents a characterization that is indispensable.

In certain situations these measurements of the quality factor $Q_0$ may become impractical due to the occurrence of resonant electron discharge phenomena, in particular during the phase of storage of energy in the resonant cavity, also known as the filling phase, during which the resonant cavity gradually stores up energy.

The resonant electron discharge (or "multipactor") phenomenon in structures under vacuum at high frequency has been known since 1936 and is described in particular in the document by J. M. R. Vaughan, "Multipactor", IEEE transaction on electron devices, vol. 35, no. 7, 1988.

The source of resonant electron discharge lies in the ability of a metallic or dielectric surface to emit one or more electrons, known as secondary electrons, when struck by an incident electron whose kinetic energy is within a particular range which will vary according to the material, typically between 0.1 and 1 kV. This phenomenon is random in nature and is defined by a statistical yield known as the secondary emission coefficient. Thus resonant electron discharge can only occur when the secondary emission coefficient is greater than 1. In addition, further conditions must also be fulfilled for resonant electron discharge to be maintained in the cavity.

In order to understand the problem posed by the resonant electronic discharge phenomenon during the characterization of the quality factor $Q_0$ of a low-loss high-frequency resonant cavity, the method for measurement of the unloaded quality factor and its constraints must be recalled.

The principle involves "filling" the resonant cavity with energy using a power generator. Once the steady-state has been achieved, the incident power is cut-off and is resonant cavity is left to empty itself. The output signal and the damping time are then measured, allowing the quality factor $Q_0$ to be calculated.

In order to carry out such measurements, the cavity is connected to two ports: an input port (called the incident port) and an output port (called the transmitted port). These ports are in general physically made up of a coaxial antenna which is introduced to a varying depth within the cavity. Each port is characterized by a coupling coefficient $\beta_e$ defined as the ratio $Q_0/Q_e$ where $Q_e$ is the external quality factor associated with the port.

The external quality factor $Q_e$ is defined as the ratio of the energy stored to the power dissipated across the port, multiplied by the pulsatance $\omega_0$ (also called the angular frequency) at resonance. Consequently the incident and transmitted ports are respectively characterized by a coupling coefficient $\beta_i$ and $\beta_t$, associated with a quality factor $Q_i$ and $Q_t$.

Thus the system in its entirety, formed by the resonant cavity connected to the antennae, exhibits an overall quality factor $Q_L$ under load where the power dissipated by the system is the sum of dissipations of the materials of the cavity and of the ports. The result, therefore, is the following relationship:

$$\frac{1}{Q_L} = \frac{1}{Q_0} + \frac{1}{Q_i} + \frac{1}{Q_t}$$

The quality factor under load $Q_L$ is measured through the decrease over time of the transmitted power $P_t$ which obeys the following relationship:

$$P_t = P_{t0} e^{-t/\tau}$$

where $\tau$ is the damping time for the cavity, which is reciprocally equivalent to the filling time for the cavity.

In practice, the transmitted port coupling is chosen to be very small, that is, the quality factor $Q_t$ is very large in comparison with $Q_0$ so that it can be neglected for the determination of the unloaded quality factor $Q_0$, such that:

$$Q_0 \approx (1+\beta_i) Q_L$$

In addition it is known that at resonance of the cavity, the coupling coefficient of the incident port $\beta_i$ is given by:

$$\beta_i = \frac{2}{\eta} - 1 \pm \sqrt{\left(\frac{2}{\eta} - 1\right)^2 - 1}$$

where $\eta$ is the ratio $P/P_i$ where P and $P_i$ represent the absorbed power and incident power respectively.

The absorbed power is obtained from the difference between the incident power and the reflected power, measured via a directional coupler. The transmitted power can be neglected due to the very low coupling coefficient $\beta_t$ being chosen.

In practice, the incident coupling coefficient $\beta_i$ is chosen to be close to 1 (so called critical coupling condition) to minimize the power reflected by the cavity and also to maximise the power absorbed by the cavity, in order to obtain a maximum amount of stored energy, i.e. for example the maximum of the accelerating gradient for an accelerating cavity, for a given power supplied by the generator. Under these conditions then, the cavity filling time can become very long in comparison with the priming time for the resonant electron discharge. This favours conditions under which resonant electronic discharge occurs.

Although the electromagnetic field in the cavity increases with time during filling, this variation remains very small, consequently preserving the resonance conditions which allow the discharge to be primed and/or be maintained during the filling phase.

In order to resolve this problem, all that is required is to choose a very large incident coupling coefficient $\beta_i$ in order to reduce the filling time and thus prevent the stable conditions for secondary electronic emissions being established.

However, by doing this the relative error in the unloaded quality factor measurement, which is directly proportional to the incident coupling coefficient $\beta_i$, becomes very large and incompatible with the desired measurement precision.

In the absence of the ability to ensure rapid filling of the cavity, various solutions have been implemented in order to attempt to overcome the resonant electron discharge phenomenon.

A first solution involves carrying out numerical simulations in order to anticipate the conditions under which resonant electron discharges occur and to geometrically modify the cavity in order to eliminate shapes which are liable to favour the occurrence of resonant electron discharges.

A second solution involves modifying the secondary emission coefficient by treating the internal surfaces of the cavity with the deposition of a thin layer or by chemical treatment.

A third solution involves applying a static magnetic or electric field where this is possible, in order to overcome the resonance conditions.

These solutions, however, introduce constraints and are only applicable during the design phase of the cavities, and are consequently not applicable to already existing cavities.

Once a resonant cavity has been constructed, there is a known process of "breaking in" the internal surfaces of the cavity during the discharge in the hope of modifying the secondary emission coefficient. In effect, as a consequence of repeated impacts by electrons, "braking in" results in desorption from the surfaces, which can modify the secondary emission coefficient.

In the case of superconducting cavities in which the very low temperatures favour the adsorption of residual gas molecules, breaking-in often takes several hours to overcome a single barrier and sometimes does not work. In this case it is still possible to carry out a heating and cooling cycle on the resonant cavity which lasts at least a day.

SUMMARY

In this context, an aspect of the present invention aims to resolve the problems listed above by proposing a device and more generally a system for characterization of the unloaded quality factor for a very low-loss resonant cavity, in particular of the superconducting type, which prevents occurrence of the "multipactor" resonant electron discharge phenomenon during characterization, thus allowing precise and rapid measurements of the unloaded quality factor of such a cavity to be made.

To this end, an embodiment of the invention proposes a device for measuring the unloaded quality factor of a resonant cavity which has an input port to accept incident power and an output port to sample and measure a portion of the energy stored in said resonant cavity, the device comprising a transmission line designed to be coupled to the input port of the resonant cavity to be characterized, which has a coupling coefficient $\beta_i$ and which is designed to transmit an incident power; wherein the device comprises a switching device (broadly termed a "switch") located upstream of the transmission line at a distance from the cavity which is equivalent to $(2n+1)\lambda_g/4$, where n is a whole number equal to or greater than zero and $\lambda_g$ the wavelength of the wave guided by the transmission line, the switching device allowing the coupling coefficient $\beta_i$ at the input port to the cavity to be modified during the measurement of the unloaded quality factor of said cavity.

The device according to an embodiment of the invention allows the resonant cavity to be filled very quickly, so as to minimize the occurrence of resonant electron discharges in the cavity by minimizing the period during which the conditions required for resonant electronic discharge to occur are met. To do this the coupling coefficient of the incident port is beneficially chosen to be very high ($\beta_i \gg 1$), and typically between 100 and 1000.

In effect, the rapid filling of the resonant cavity means that the energy of the electrons, and consequently the conditions liable to favour the occurrence and maintenance of resonant electron discharge in the cavity, can be quickly modified. Thus, thanks to the rapid filling of the resonant cavity the period during which the secondary emission coefficient is greater than 1 is minimized and conditions of very high energies are quickly achieved.

On the other hand, the measurement of the quality factor is achieved with a low coupling coefficient of the incident port ($1 \ll \beta_i$), typically between 0.1 and 0.01, so as not to adversely affect the precision of the measurement of the unloaded quality factor.

The switching of the coupling coefficient of the incident port is achieved thanks to the rapid switching device placed upstream of the transmission line and at a distance which is equivalent to an odd multiple of a quarter of the guided wavelength.

Thus the device according to an embodiment of the invention allows very rapid short-circuiting (i.e. in a very short time relative to the damping time) of the input port by re-establishing a very low impedance through the transmission line. It should be recalled that the damping time is equivalent to the time required for the energy stored in the resonator to decrease by 63.2% once the power generator is shut-off or isolated.

A benefit of the switching is to modify the coupling coefficient between the filling phase and the damping phase by at least a factor of $10^3$. Thus, by way of an example, the coupling coefficient $\beta_i$, with a value typically between 100 and 1000 during the cavity filling phase, very rapidly changes (in less than 10 microseconds) to a value typically between 0.01 and 0.1 during the course of the damping phase.

An embodiment of the invention also has the benefit of guaranteeing a measurement precision equivalent to that likely to be achieved with a critical coupling on the incident port, i.e. with an incident coupling factor equal to 1.

The device according to an embodiment of the invention may also exhibit one or more of the following characteristics, taken individually or according to all technically possible combinations:

the switching device exhibits a switching time which changes the coupling coefficient $\beta_i$ at the input port (2) of the cavity which is equal to or less than $1/10$ of the damping time, and for example equal to or less than $1/100$ of the damping time;

the switching device exhibits a switching time which changes the coupling coefficient $\beta_i$ at the input port of the cavity which is equal to or less than 10 microseconds;

the switching device changes the coupling coefficient $\beta_i$ at the input port of the cavity by at least a factor of $10^3$;

the switching device is made from a PIN diode placed in series or from at least two PIN diodes placed in series;

the coupling coefficient $\beta_i$ of the transmission line at the input port to the cavity is greater than 100 when the switching device is closed;

the coupling coefficient $\beta_i$ of the transmission line at the input port to the cavity is less than 0.1 when the switching device is open;

Another aspect of the invention is directed to a system for measuring the unloaded quality factor of a resonant cavity, wherein the system comprises:

a power generator which generates an incident power which is designed to fill the resonant cavity with energy;

a measurement device according to an embodiment of the invention;

a resonant cavity to be characterized which comprises an input port to receive the incident power and an output port to sample and measure a portion of the energy stored in the cavity.

Another aspect of the invention is directed to a method for measuring the unloaded quality factor of a resonant cavity using the measurement system according to an embodiment of the invention wherein the method comprises:

a step for storage of the energy provided by the generator in the cavity;

a step for switching the switching device, changing from a closed state to an open state when the steady state of the cavity is achieved and which modifies the coupling coefficient $\beta_i$ at the input port to the cavity;

a step for sampling and for measurement of a portion of the energy stored in the resonant cavity;

a step for determining the unloaded quality factor of the resonant cavity.

BRIEF DESCRIPTION OF FIGURES

Other characteristics and benefits of the invention will emerge more clearly from the description of it that is given below, by way of an indication and which is in no way restrictive, with reference to the appended figures in which.

DETAILED DESCRIPTION

Figure 1:
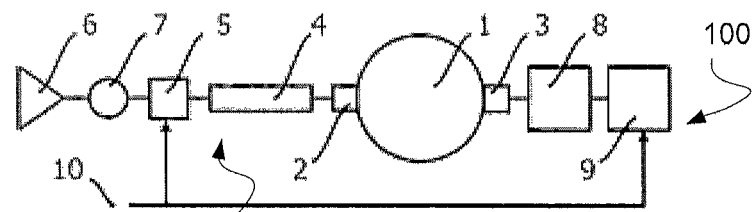
FIG. 1 is a block diagram of a system for measuring the unloaded quality factor of a resonant cavity according to an embodiment of the invention.

FIG. 1 is a block diagram showing the system 100 for characterization of unloaded quality factor $Q_0$ of a resonant cavity 1 of the superconducting type.

The system 100 in particular comprises:
a resonant cavity 1 which has an input port 2 (incident port) and an output port 3 (transmitted port);
a power generator 6 used to fill the resonant cavity 1;
a device 110 according to an embodiment of the invention comprising: a fast switch 5 controlled by an operating signal; and a so-called quarter-wave transmission line 4 separating the switch 5 from the resonant cavity 1.

The transmission line 4 beneficially has a length L equivalent to an odd multiple of the wavelength guided in the transmission line 4, that is:

$$L=(2n+1)\lambda_g/4$$

Where n is a whole number greater than or equal to 0 and $\lambda_g$ is the wavelength of the wave guided in the transmission line 4.

It is desirable that the so-called quarter-wave transmission line chosen meets a minimum-loss criterion. This transmission line is beneficially made of a coaxial cable which exhibits losses of less than 0.1 dB/m. The whole number n of the length of the transmission line chosen will desirably be zero whenever the overall dimensions and measurement configuration allows.

This transmission line 4 connects the input port 2 of the resonant cavity 1 to the switch 5 placed in series as shown in FIG. 1. The switch 5 is supplied by a power generator 6 through a circulator 7 placed between the switch 5 and the power generator 6.

The switch 5 is a fast switch which allows the change from a closed state to an open state to be rapidly achieved (i.e. with a switching time equal to or less than $1/10$ of the damping time and beneficially equal to or less than $1/100$ of the damping time) by changing the coupling coefficient $\beta_i$ of the incident port. According to an embodiment of the invention, the switch 5 exhibits a switching time which is equal to or less than 10 µs.

When the switch 5 is closed, the coupling coefficient $\beta_i$ of the incident port, typically with a value of between 100 and 1000, is determined solely by the geometry of the transmission line coupler at the input port 2 to the cavity 1, i.e. the penetration length of the antenna for electrical coupling or the surface area of the loop for inductive coupling in the case of an implementation using a coaxial line.

When switch 5 is open, the latter exhibits a leakage impedance which is beneficially high placed in series with the source impedance of the generator 6 (or load impedance) known as $Z_L$ to represent the sum of the two impedances. Thus the resulting impedance at the incident port is equivalent to:

$$Z_i = \frac{Z_0^2}{Z_L}$$

where $Z_0$ is the characteristic impedance of the transmission line, typically equal to 50Ω. Thus, by way of an example, if the sum of the two impedances $Z_L$ is equal to 500 kΩ, then the impedance resulting at the input port would be 5 mΩ when the switch 5 is open, which more or less amounts to short-circuiting of the input port.

As a result of the fast switch 5 of the system according to an embodiment of the invention allowing switching between the two states (closed and open) to be performed, resulting in a transformation of impedance in the transmission line (i.e. into a short-circuit state), the system according to an embodiment of the invention allows a very low ($\beta_i \ll 1$) coupling coefficient $\beta_i$ for the incident port 2 to be achieved during the damping phase. Thus by minimizing the coupling coefficient of the incident port ($\beta_i \ll 1$), as a result of the rapid switching of the switch a quality factor under load $Q_L$ is obtained that is substantially equivalent to the unloaded quality factor $Q_0$ of the resonant cavity 1, with a relative error reduced to $2\Delta P/P$, where $\Delta P/P$ represents the relative error for the power measurements.

The quality factor under load $Q_L$ is measured through the decrease over time in the transmitted power $P_t$ which obeys the following relationship:

$$P_t = P_{t0} e^{-t/\tau}$$

where $\tau$ is the damping time for the cavity, which is reciprocally equivalent to the filling time for the cavity.

The measurement of the decrease in the energy stored in the cavity 1 is performed, for example, using a diode detector 8, on the very weakly coupled transmitted port. The measurement allows the damping time to be determined and then the unloaded quality factor $Q_0$ of the cavity to be determined, for example using an oscilloscope 9 triggered by the pulsed control signal for switch 5. According to another embodiment which is not shown, the diode detector 8 and the oscilloscope 9 may be replaced by a spectral analyser configured in time-swept mode.

Figure 2:
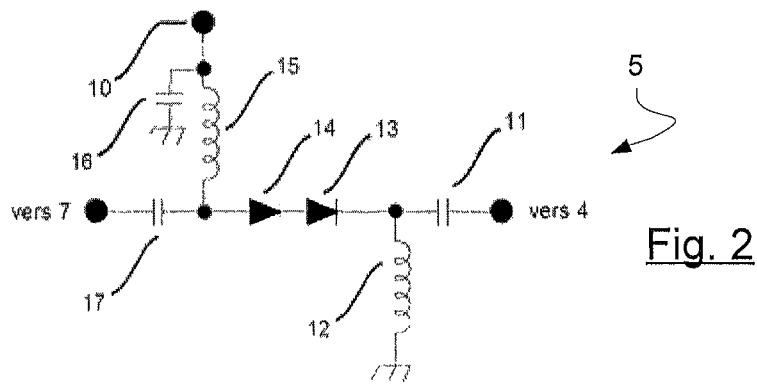
FIG. 2 shows an electrical circuit diagram for the device for switching the measurement system according to an embodiment of the invention.

FIG. 2 shows an embodiment of the fast switch 5 of the system 100 according to an embodiment of the invention.

The fast switch 5 is made from at least one Positive Intrinsic Negative (or PIN) diode, known as Single Pole Single Through (or SPST), or several PIN diodes placed in series in order to achieve the desired levels of performance and results. In general each of the components of the switch 5 is chosen in an appropriate manner, depending on the resonance frequency of the cavity 1, on the peak and mean power to the transmitted to cavity 1 as well as on the order of the estimated unloaded quality factor $Q_0$.

The fast switch 5 is controlled at input 10 by a pulse generator which generates the control signal for the switch 5. The electrical characteristics of the pulse generator should be compatible with the specifications of the PIN diodes chosen. By way of an example, for MA4P700 type diodes, the positive voltage applied is typically 10 V and the current supplied must be at least 100 mA for the closed position of the switch. The closed position of the switch 5 therefore results in a high coupling coefficient $\beta_i$ for the filling phase of the resonant cavity 1. In order to change from the closed position of the switch 5 to the open position, the pulse generator applies a negative voltage of −30 V to input 10, which results in a lower coupling coefficient $\beta_i$ during the damping phase, which corresponds to the measurement phase of the unloaded quality factor.

According to the embodiment shown in FIG. 2, the switch 5 has two diodes 13 and 14 in series. The switch 5 may, however, comprise a diode placed in series in relation to the signal, or several diodes in series in relation to the signal. The number of diodes in series is determined so as to achieve a variation in the coupling coefficient $\beta_i$ by a factor which is equal to or greater than $10^3$.

The capacitances 11 and 17 are used to decouple the control signal 10 in relation to the resonant cavity 1 and the power generator 6. Reciprocally, the inductances 12 and 15 stop high frequency currents in relation to earth and to the pulse generator which generates the switch 5 control signal. The capacitance 16 serves to dampen the over-voltages generated by the inductances during the switching of the switch 5.

Figure 3:
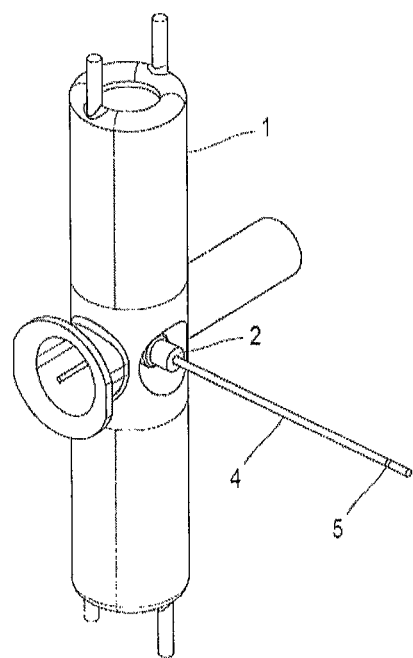
FIG. 3 is a perspective view of an example of a resonant cavity which may be characterized by the system according to an embodiment of the invention.

Thus, by way of an example, for a superconducting cavity shown in FIG. 3 used to accelerate deuterium nuclei, and which exhibits a resonance frequency at 175 MHz, which needs an incident power of 2 kW (peak and mean), which exhibits a quality factor $Q_0$ estimated at $10^9$, and by representing each PIN diode by its equivalent circuit as a function of their state: a series resistance of 0.8Ω when it conducts (during the filling phase) and a resistance in parallel of 200 kΩ with a capacitance of 0.7 pF when it is shut off (measurement phase), the quality factor of the input port $Q_i$ with such a switch is of the order of $10^6$ during the filling phase and of the order of $10^{10}$ when the diodes are shut off during the measurement phase, that is, a ratio of the order of $10^4$ between the two switching states of the switch.

Thus the system according to the invention prevents the priming of resonant electron discharge by minimizing the filling time of the cavity 1, of the order of 1 millisecond, so that the field in the cavity 1 may increase sufficiently rapidly not to offer stable conditions for priming of resonant electron discharge.

The invention claimed is:

1. A device for measuring the unloaded quality factor of a resonant cavity which has an input port to receive incident power and an output port for sampling and for measuring a portion of energy stored in the resonant cavity, said device comprising:
    a transmission line to be coupled to the input port of said resonant cavity to be characterized, exhibiting a coupling coefficient $\beta_i$ and designed to transmit incident power; and
    a switch configured to allow switching between only two states of the switch, the switching between the two states inducing a transformation of impedance in the transmission line, said switch being placed upstream of the transmission line at a distance from the resonant cavity equivalent to $(2n+1)\lambda_g/4$, where n is a whole number greater than or equal to zero and $\lambda_g$ the wavelength of the wave guided by said transmission line, said switch having a switching time between the two states for modifying the coupling coefficient $\beta_i$ at the input port of the resonant cavity that is equal to or less than ¹⁄₁₀ of a damping time during measurement of the unloaded quality factor of said resonant cavity.

2. The device for measuring the unloaded quality factor of a resonant cavity according to claim 1, wherein the switch has a switching time for modifying the coupling coefficient $\beta_i$ at the input port of the cavity which is equal to or less than 10 microseconds.

3. The device for measuring the unloaded quality factor of a resonant cavity according to claim 1, wherein the switch modifies the coupling coefficient $\beta_i$ at the input port of the cavity by at least a factor of $10^3$.

4. The device for measuring the unloaded quality factor of a resonant cavity according to claim 1, wherein the switch is made from a PIN diode placed in series with the transmission line or from at least two PIN diodes placed in series with the transmission line.

5. The device for measuring the unloaded quality factor of a resonant cavity according to claim 1, wherein the coupling coefficient $\beta_i$ of the transmission line at the input port of the cavity is greater than 100 when the switch is closed.

6. The device for measuring the unloaded quality factor of a resonant cavity according to claim 1, wherein the coupling coefficient $\beta_i$ of the transmission line at the input port of the cavity is less than 0.1 when the switch is open.

7. A system for measuring the unloaded quality factor of a resonant cavity, wherein said system comprises:
   a power generator configured to generate an incident power which is designed to fill said resonant cavity with energy;
   a measuring device according to claim 1;
   a resonant cavity to be characterized which comprises an input port to receive the incident power and an output port to sample and measure a portion of the energy stored in the cavity.

8. A method for measuring the unloaded quality factor of a resonant cavity using a measurement system, said measurement system comprising
   a power generator configured to generate an incident power which is designed to fill said resonant cavity with energy;
   a measuring device that has an input port to receive incident power and an output port for sampling and for measuring a portion of energy stored in the resonant cavity, said measuring device comprising:
      a transmission line to be coupled to the input port of said resonant cavity to be characterized, exhibiting a coupling coefficient $\beta_i$ and designed to transmit incident power; and
      a switch configured to allow switching between only two states of the switch, the switching between the two states inducing a transformation of impedance in the transmission line, said switch being placed upstream of the transmission line at a distance from the resonant cavity equivalent to $(2n+1)\lambda_g/4$, where n is a whole number greater than or equal to zero and $\lambda_g$ the wavelength of the wave guided by said transmission line, said switch having a switching time between the two states for modifying the coupling coefficient $\beta_i$ at the input port of the resonant cavity that is equal to or less than $1/10$ of a damping time during measurement of the unloaded quality factor of said resonant cavity, wherein said method comprises:

storing the energy provided by the generator in said cavity;

switching the switch changing from a closed state in which the switch is closed to an open state in which the switch is open when the steady state of the cavity is achieved and which modifies the coupling coefficient $\beta_i$ at the input port to the cavity;

sampling and measuring a portion of the energy stored in the resonant cavity;

determining the unloaded quality factor of said resonant cavity.

* * * * *